(12) United States Patent
Dobschal

(10) Patent No.: US 9,703,018 B2
(45) Date of Patent: Jul. 11, 2017

(54) LENS WITH AN EXTENDED RANGE OF FOCUS

(75) Inventor: Hans-Jürgen Dobschal, Kleinromstedt (DE)

(73) Assignee: CARL ZEISS AG, Oberkochen (DE)

( * ) Notice: Subject to any disclaimer, the term of this patent is extended or adjusted under 35 U.S.C. 154(b) by 777 days.

(21) Appl. No.: 14/118,539

(22) PCT Filed: May 16, 2012

(86) PCT No.: PCT/EP2012/002098
§ 371 (c)(1),
(2), (4) Date: May 19, 2014

(87) PCT Pub. No.: WO2012/156081
PCT Pub. Date: Nov. 22, 2012

(65) Prior Publication Data
US 2014/0293426 A1    Oct. 2, 2014

(30) Foreign Application Priority Data

May 18, 2011    (DE) .................. 10 2011 101 899

(51) Int. Cl.
*G02B 5/18*    (2006.01)
*G02B 3/10*    (2006.01)
(Continued)

(52) U.S. Cl.
CPC .............. *G02B 3/10* (2013.01); *A61F 2/1632* (2013.01); *G02B 3/0087* (2013.01); *G02B 3/02* (2013.01);
(Continued)

(58) Field of Classification Search
CPC .............. G02B 27/4211; G02B 5/1866; G02B 5/1861; G02B 27/0037; G02B 5/1814;
(Continued)

(56) References Cited

U.S. PATENT DOCUMENTS 5,982,543 A    11/1999    Fiala
6,120,148 A    9/2000    Fiala et al.
(Continued)

FOREIGN PATENT DOCUMENTS

DE    36 17 363 A1    11/1987
DE    101 61 329 A1    7/2002
(Continued)

OTHER PUBLICATIONS

Prasad et al., "Pupil-phase optimization for extended-focus, aberration-corrected imaging systems," *Proceedings of the SPIE Advanced Signal Processing Algorithms, Architectures, and Implementations XIV*, SPIE, US, 5559:335-345, (2004).
(Continued)

*Primary Examiner* — Scott J Sugarman
*Assistant Examiner* — Sharrief Broome
(74) *Attorney, Agent, or Firm* — Alston & Bird LLP

(57) ABSTRACT

The invention relates to a lens which has an extended range of focus, wherein the lens consists of a solid material, the optical surfaces of the lens are transparent and the lens has a focal power distribution. According to the invention, the focal power distribution $F_G$ of the lens (1), in relation to a plane perpendicular to the optical axis (10), changes as a function of the radial height r and of the azimuth angle phi of the aperture between a base value of the focal power $F_L$ not equal to zero and a maximum value $F_{Smax}$. Hence, the focal power distribution emerges as $F_G(r,\text{phi}) = F_L + F_S(r,\text{phi})$, with the spiral focal power component $F_S(r,\text{phi}) = F_{Smax}(r) * w(\text{phi})$, where $F_{Smax}(r)$ depends nonlinearly on the radius and w(phi) is a factor for the focal power component with a spiral profile.

12 Claims, 5 Drawing Sheets

(51) Int. Cl.
| | |
|---|---|
| *G02B 27/00* | (2006.01) |
| *G02C 7/06* | (2006.01) |
| *A61F 2/16* | (2006.01) |
| *G02B 3/02* | (2006.01) |
| *G02B 3/00* | (2006.01) |
| *G02C 7/02* | (2006.01) |

(52) U.S. Cl.
CPC ....... *G02B 5/1866* (2013.01); *G02B 27/0075* (2013.01); *G02C 7/024* (2013.01); *G02C 7/061* (2013.01); *G02B 2003/0093* (2013.01); *G02B 2005/1804* (2013.01); *G02C 2202/20* (2013.01)

(58) Field of Classification Search
CPC .. G02B 5/1895; G02B 5/1809; G02B 5/1847; G02B 5/1857; G02B 27/4272; G02B 27/4277; G02B 5/18; G02B 5/1852; G02B 5/1871; G02B 5/1876; G02B 6/1241; G02B 1/01
USPC ....... 359/574, 569, 576, 571, 572, 573, 565, 359/489.06, 567
See application file for complete search history.

(56) References Cited

U.S. PATENT DOCUMENTS

| | | |
|---|---|---|
| 6,536,899 B1 | 3/2003 | Fiala |
| 2003/0117577 A1 | 6/2003 | Jones et al. |
| 2006/0176572 A1 | 8/2006 | Fiala |
| 2010/0002310 A1 | 1/2010 | George et al. |
| 2010/0329605 A1 | 12/2010 | Graham |

FOREIGN PATENT DOCUMENTS

| | | | |
|---|---|---|---|
| IL | WO 2008087486 A2 * | 7/2008 | ......... G02B 27/0068 |
| WO | WO 03/054616 A2 | 7/2003 | |
| WO | WO 2008/087485 A2 | 7/2008 | |
| WO | WO 2008/087486 A2 | 7/2008 | |
| WO | WO 2010/083546 A2 | 7/2010 | |

OTHER PUBLICATIONS

Prasad et al., "Engineering the pupil phase to improve image quality," Proceedings of the SPIE, SPIE, US, 5108:1-12, (2003).
PCT International Search Report for application PCT/EP2012/002098 mailed Aug. 27, 2012.
PCT International Preliminary Report on Patentability for application PCT/EP2012/002098 mailed Nov. 28, 2013.

* cited by examiner

LENS WITH AN EXTENDED RANGE OF FOCUS

CROSS-REFERENCE TO RELATED APPLICATIONS

This is a national stage application filed under 35 U.S.C. §371 based on International Patent Application No. PCT/EP2012/002098, filed May 16, 2012. This application also claims priority under 35 U.S.C. §119 to German Patent Application No. 10 2011 101 899.2, filed May 18, 2011. The entire contents of all of the above-identified patent applications are expressly incorporated herein by reference.

The invention relates to a lens which has an extended range of focus, wherein the lens consists of a solid material, the optical surfaces of the lens are transparent and the lens has a focal power distribution. The invention furthermore relates to a method for producing the lens and to a method for influencing the imaging of an image onto the retina and to a lens system with an extended range of focus.

Multifocal lenses should simultaneously meet a number of demands. Initially, a sufficiently good contrast transfer function in two or more focal planes should be ensured. Furthermore, the contrast transfer function should be independent of the size of the pupil. And finally, it should be easy to produce the lens; it should not have projections or edges, and therefore have curves which are as smooth as possible.

Such lenses are used, in particular, for correcting visual defects by means of spectacle lenses or as intraocular lenses (IOLs). In contrast to the monofocal IOLs, which were already introduced many years ago, multifocal lenses were previously only implemented for the bifocal case since there are significant problems in satisfying the aforementioned demands simultaneously. Here, a variant is based upon a special rotationally symmetric ring system, wherein there is sufficiently good imaging for two discrete object-side focal planes, for example at 0 dpt and at a corrective power of approximately 3 dpt, by skillful matching of ring radii, ring widths and ring depths.

Such a bifocal lens is described in the patent document U.S. Pat. No. 5,982,543 A and uses a rotationally symmetric Fresnel-like ring system.

U.S. Pat. No. 6,120,148A describes a rotationally symmetric diffractive ring system. The bifocal lens from U.S. Pat. No. 6,536,899 B likewise utilizes a ring system, wherein each ring consists of two sub-rings, which respectively realize the two desired focal lengths.

In a slightly modified form, solutions are also derived herefrom, in which a single lens covers an extended continuous range of focus. Such lenses are also known by the term "extended depth of focus lens" or else as "EDoF lens". In US 2006176572 A, use is made of a rotationally symmetric system of rings, wherein the individual focal lengths of the rings lie within the desired continuous focal length range. The "extended depth of focus" effect is created by mixing the various focal lengths.

The system in accordance with WO 100 835 46A consists of sectors ("pie slices") with a focal power increasing in the azimuth direction. Here, the focal power distribution has discrete steps between the sectors.

US20100002310 A1 describes an optical imaging system for a camera which has an extended depth of field range. The extended depth of field is achieved by a combination of several lenses with aspherical surfaces.

The object of the invention consists of developing a new lens with an extended range of focus. The new lens should provide, either individually, in particular as an intraocular lens, or in conjunction with other optical components, optical systems which, while having a sufficiently good imaging quality, provide a large depth of field range and can be produced in a cost-effective manner.

According to the invention, for the new lens, the object of the invention is achieved by the features of claim 1. According to the invention, for the new lens, the object of the invention is achieved by the features of claim 2. According to the invention, in the method for producing the lens, the object of the invention is achieved by the features of claim 11. Advantageous developments of the invention are the subject matter of the dependent claims. According to the invention, in the method for influencing the imaging of an image onto the retina, the object of the invention is achieved by the features of claim 15. According to the invention, in a lens system with an extended range of focus, the object of the invention is achieved by the features of claim 16.

The invention relates to a lens with an extended range of focus, wherein the lens consists of a solid, transparent material and has two manufactured optical surfaces. The lens has a focal power distribution $F_G$ which, in relation to a plane perpendicular to the optical axis, changes as a function of the radial height r and of the azimuth angle phi of the aperture between a base value of the focal power $F_L$ not equal to zero and a maximum value $F_{Smax}$. Hence, the focal power distribution emerges as $$F_G(r,\text{phi}) = F_L + F_S(r,\text{phi}),$$

where
$F_S(r, \text{phi}) = F_{Smax}(r) * w(\text{phi})$ is a spiral focal power component. In the formula $F_S(r, \text{phi}) = F_{Smax}(r) * w(\text{phi})$, $F_{Smax}(r)$ depends nonlinearly on the radius and w(phi) is a factor for the focal power component with the spiral profile, which, in general, is described by the formula $$w(phi) = \sum_{i=1}^{M} I_i \exp[-a_i(phi - w_i)^2],$$

where $w_i$ are the peak positions in the angular distribution function; $I_i$ are intensity values of the individual peaks; $a_i > 0$ are damping coefficients for the respective peak positions and i is a counter and M≥i is a final value.

The invention furthermore relates to a lens with an extended range of focus, wherein the lens consists of a solid, transparent material and has two manufactured optical surfaces. The lens has a focal power distribution $F_G$ which, in relation to a plane perpendicular to the optical axis, changes as a function of the radial height r and of the azimuth angle phi of the aperture between a base value of the focal power $F_L$ not equal to zero and a maximum value $F_{Smax}$. Hence, the focal power distribution emerges as $$F_G(r,\text{phi}) = F_L + F_S(r,\text{phi}),$$

where
$F_S(r, \text{phi}) = F_{Smax}(r) * w(\text{phi})$ is a spiral focal power component.

In the formula $F_S(r, \text{phi}) = F_{Smax}(r) * w(\text{phi})$, $F_{Smax}(r)$ depends nonlinearly on the radius and w(phi) is a factor for the focal power component with the spiral profile, which is described as a linear profile by the formula $$w(phi) = \frac{phi}{2\pi}.$$

The lens is distinguished by virtue of the fact that the maximum focal power $F_{Smax}(r)$ depends nonlinearly on the radius and is described by the polynomial formulae $$F_{Smax}(r) = \sum_{j=2}^{N} c_j * r^j$$

or $$F_{Smax}(r) = \sum_{j=1}^{N} c_j * r^{2*j},$$

with the polynomial coefficients $c_j$ for a refractive focal power and $$F_{Smax}(r) = \sum_{j=2}^{N} k_j * r^j$$

or $$F_{Smax}(r) = \sum_{j=1}^{N} k_j * r^{2*j},$$

with the polynomial coefficient $k_j$ for a diffractive focal power, where j is a counter and N≥j is a final value.

In order to obtain further degrees of freedom for dimensioning the lens, the maximum focal power $F_{Smax}$ depends nonlinearly on the radius and is additionally dependent on the azimuth angle phi of the aperture. The following polynomial formulae apply in this case:

$$F_{Smax}(r, phi) = \sum_{j=2}^{N} c_j(phi) * r^j$$

or $$F_{Smax}(r, phi) = \sum_{j=1}^{N} c_j(phi) * r^{2*j},$$

with the polynomial coefficients $c_j$ for a refractive focal power and $$F_{Smax}(r, phi) = \sum_{j=2}^{N} k_j(phi) * r^j$$

or $$F_{Smax}(r, phi) = \sum_{j=1}^{N} k_j(phi) * r^{2*j},$$

with the polynomial coefficient $k_j$ for a diffractive focal power, where j is a counter and N≥j is a final value.

In a first case, the focal power distribution $F_G(r, phi)$ of the lens emerges from a height profile $z_G(r, phi)$ of a second optical surface to be manufactured. The shape of the surface to be manufactured emerges from adding the height profile $z_L(r)$ of a calculated base surface and a height profile $z(r, phi)$, where $$F_G(r, phi) = F_L + F_S(r, phi)$$
$$= z_G(r, phi)$$
$$= z_L(r) + z(r, phi)$$

applies. The additive height z(r, phi) changes nonlinearly dependent on the radius, starting from zero to a maximum value $z_{max}(r)$ which supplies the maximum focal power $F_{Smax}(r)$, and emerges as a function $$z(r, phi) = z_{max}(r) * w(phi),$$

with $$z_{max}(r) = \sum_{j=2}^{N} c_j * r^j$$

or $$z_{max}(r) = \sum_{j=1}^{N} c_j * r^{2*j},$$

where the radius r changes continuously between 0 and D/2 and the azimuth angle phi of the aperture changes continuously between 0 and $2\pi$, as a result of which the optical surface to be manufactured is described by the spiral height profile.

In an alternative variant, the additive height z(r, phi) changes nonlinearly dependent on the radius and dependent on the azimuth angle phi of the aperture, starting from zero to a maximum value $z_{max}(r, phi)$ which supplies the maximum focal power $F_{Smax}(r, phi)$, and emerges as a function $$z(r, phi) = z_{max}(r, phi) * w(phi),$$

with $$z_{max}(r, phi) = \sum_{j=2}^{N} c_j(phi) * r^j$$

or $$z_{max}(r, phi) = \sum_{j=1}^{N} c_j(phi) * r^{2*j}.$$

In a second case, the focal power component with the spiral profile $F_S(r, phi)$ emerges from the effect of an optical grating applied to a manufactured second optical surface with the focal power $F_L$, where $$F_G(r,phi)=F_L+F_S(r,phi)=F_L+\text{Phase}(r,phi)$$

applies. The frequency of the optical grating changes nonlinearly dependent on the radius, starting from a base value zero to a maximum value $\text{Phase}_{max}$ which supplies the maximum focal power $F_{Smax}$. The following applies to the spiral focal power profile:

$$F_S(r, phi) = F_{Smax}(r) * w(phi)$$
$$= \text{Phase}(r, phi)$$
$$= \text{Phase}_{max}(r) * w(phi),$$

-continued with $$\text{Phase}_{max}(r) = \sum_{j=2}^{N} k_j * r^j$$

or $$\text{Phase}_{max}(r) = \sum_{j=1}^{N} k_j * r^{2*j},$$

where the radius r changes continuously between 0 and D/2 and the azimuth angle phi of the aperture changes continuously between 0 and $2\pi$, as a result of which the optical grating has a spiral phase profile.

In an alternative variant, the frequency of the optical grating changes nonlinearly dependent on the radius and is dependent on the azimuth angle phi of the aperture, starting from a base value zero to a maximum value $\text{Phase}_{max}$ which supplies the maximum focal power $F_{Smax}(r, phi)$. The following applies to the spiral focal power profile:

$$F_S(r, phi) = F_{Smax}(r, phi) * w(phi)$$
$$= \text{Phase}(r, phi)$$
$$= \text{Phase}_{max}(r, phi) * w(phi),$$

with $$\text{Phase}_{max}(r, phi) = \sum_{j=2}^{N} k_j(phi) * r^j$$

or $$\text{Phase}_{max}(r, phi) = \sum_{j=1}^{N} k_j(phi) * r^{2*j}.$$

In a third case, the focal power component with the spiral profile $F_S$ emerges from an additive or subtractive refractive index distribution $\Delta n(r, phi)$, wherein the material of the lens has a refractive index distribution which changes nonlinearly dependent on the radius, starting from a base value $n_2$ to a maximum value $\Delta n_x$, where $$F_G(r,phi) = F_L + F_S(r,phi) = F_L + \Delta n(r,phi)$$

applies and the following applies to the spiral focal power profile:

$$F_S(r, phi) = F_{Smax}(r) * w(phi)$$
$$= \Delta n(r, phi)$$
$$= \Delta n_{max}(r) * w(phi),$$

with $$\Delta n_{max}(r) = \sum_{j=2}^{N} c_j * r^j$$

or $$\Delta n_{max}(r) = \sum_{j=1}^{N} c_j * r^{2*j},$$

where the radius r changes continuously between 0 and D/2 and the azimuth angle phi of the aperture changes continuously between 0 and $2\pi$, as a result of which a spiral refractive index distribution of the lens material is described.

In an alternative variant, the material of the lens (1) has a refractive index distribution, which changes nonlinearly dependent on the radius and dependent on the azimuth angle phi of the aperture, starting from a base value $n_2$ to a maximum value $\Delta n_{max}$, where $$F_G(r,phi) = F_L + F_S(r,phi) = F_L + \Delta n(r,phi)$$

applies and the following applies to the spiral focal power profile:

$$F_S(r, phi) = F_{Smax}(r, phi) * w(phi)$$
$$= \Delta n(r, phi)$$
$$= \Delta n_{max}(r, phi) * w(phi),$$

with $$\Delta n_{max}(r, phi) = \sum_{j=2}^{N} c_j(phi) * r^j$$

or $$\Delta n_{max}(r, phi) = \sum_{j=1}^{N} c_j(phi) * r^{2*j}.$$

The above-described variants provide special new lens shapes, by means of which it is possible to cover simultaneously a predetermined focal length range, i.e. it is possible to generate a sufficiently good image quality over an extended range of focus.

Such lenses with an extended range of focus find use in optical systems for a camera, a microscope or optical measurement systems.

A main field of application is an intraocular lens with a variable focal length range, which realizes a focusing range from 0 to approximately 3.5 dpt in relation to a fixed base focal power. Such an intraocular lens is usually implanted into the eye after removing the natural lens. However, it can also be used in addition to the natural lens. Provision is also made for impressing or working a spiral focal power distribution into the natural eye lens.

The lens according to the invention is produced by the following steps:

Step 1: Calculating a monofocal base system with a basic focal power $F_L$ while setting the parameters of a first optical surface, the parameters of an optical base surface and a lens thickness d as well as a material type with a refractive index and an Abbe number.

Step 2: Adding or subtracting an additional focal power distribution $F_S(r, phi)$ which, in relation to a plane perpendicular to the optical axis, changes nonlinearly depending on the radius as a function of the radial height r and of the azimuth angle phi of the aperture between a base value and a maximum value $F_{Smax}(r)$ or $F_{Smax}(r, phi)$, as a result of which the additional focal power $F_S(r, phi)$ is distributed over the base surface in a spiral changing manner.

Step 3: Producing the spiral focal power distribution at the lens and/or on the lens and/or within the lens.

"Adding" the spiral focal power distribution can be brought about by several variants, which can each be used individually or together in any combination:

a) "Adding" a spiral height profile z(r, phi) to one of the surfaces of the lens calculated in step 1, which is the base surface, wherein this fixes the profile of the second optical surface.

The lens according to the invention is produced by a method in which the additional focal power distribution $F_S(r,$ phi), which changes between the base value and the maximum value, is generated by adding a spiral height profile z(r, phi) to the calculated base surface of the base system, wherein the additive height z is a function of the radius r and of the azimuth angle phi of the aperture. Here, the additive height z changes nonlinearly dependent on the radius between the value zero and a maximum value $z_{max}(r)$ or $z_{max}(r, phi)$. Hence this fixes a spiral height profile of the second optical surface to be manufactured.

b) "Adding" a spiral diffractive structure to one of the calculated surfaces of the lens in accordance with step 1.

In this case, the additional focal power distribution $F_S(r, phi)$, which changes between the base value and the maximum value, is generated by adding the effect of a spiral grating profile Phase(r, phi) to the manufactured second optical surface. Here, the manufactured second optical surface corresponds to the calculated base surface and the grating profile is a function of the radius r and of the azimuth angle phi of the aperture. The refractive effect changes nonlinearly dependent on the radius between the value zero and the maximum value $Phase_{max}(r)$ or $Phase_{max}(r, phi)$. Hence, the spiral optical grating is applied to the manufactured optical surface.

c) "Adding" a spiral refractive index distribution in the material of the lens. In this case, the calculated surfaces in accordance with step 1 are not modified. The second optical surface corresponds to the base surface.

The focal power distribution $F_S(r, phi)$, which changes nonlinearly dependent on the radius between the base value and the maximum value $\Delta n_{max}(r)$ or $\Delta n_{max}(r, phi)$, is produced by a spiral refractive index distribution $\Delta n(r, phi)$ in the material of the lens.

Step 3, which is referred to above and relates to the real physical production of the lens according to the invention, contains the production of the first optical surface and of the second optical surface as well as the spiral refractive index distribution at and/or on and/or within the lens.

The production methods for optical lenses which, in conjunction with the invention, can also have at least one non-spherical surface are known. In particular, these are:

aa) producing a height profile of the optical surfaces by hot stamping or injection molding
ab) producing a height profile of the optical surfaces by diamond turning
ba) producing a diffractive structure by lithographic etching methods on the second optical surface
bb) producing a diffractive structure by diamond turning on the second optical surface
ca) producing a refractive index gradient by centrifugal casting from the liquid state
cb) producing a refractive index gradient by ion implantation.

Naturally, the variants a) and/or b) can also be applied to both optical surfaces of a lens in a manner subdividing the effect. Diffractive optical elements can be used additionally or together with the generation of the focal power distribution for color correction. The scope of the invention also includes other methods and measures, by means of which the spiral focal power distribution according to the invention can be obtained in a lens, for example by the introduction of nanoparticles.

As a result of the above-described procedure, a continuous variation of the additional focal power to the focal power of the base system of between 0 and approximately 3.5 dpt is achieved in e.g. an intraocular lens with, in many cases of application, a sufficiently good image quality.

The radius-dependent and azimuth angle-dependent focal power $F_G(r, phi)$ emerges from the sum of a basic focal power of the base system $F_L$ and the additional focal power $F_S(r, phi)$ which is dependent on the radius and the angle:

$$F_G(r, phi) = F_L + F_S(r, phi)$$
$$= \frac{1}{f_L} + \frac{1}{f_S(r, phi)}.$$

Since standardized optical methods are used for producing the lens with the extended range of focus, this lens can be produced in a cost-effective manner.

In the case a) of "adding" a spiral height profile to one of the optical surfaces of the lens and thereby realizing a spiral focal power distribution of the overall system, the following observations apply:

The overall focal power $F_G$ is composed by adding the basic focal power of the base system $F_L$ to the additional focal power $F_S$.

$$F_G(r,phi)=F_L+F_S(r,phi),$$

where the spiral focal power component is $$F_S(r,phi)=F_{Smax}(r,phi)*w(phi).$$

Since the distribution of the additional focal power in this case is achieved by a radial height distribution, $$F_G(r, phi) = F_L + F_S(r, phi)$$
$$= z_G(r, phi)$$
$$= z_L(r) + z(r, phi)$$

applies. The height profile, which supplies the spiral additional focal power, is, in general, described by $$z(r,phi)=z_{max}(r,phi)*w(phi).$$

The basic focal power of the base system emerges for spherical lenses from the formula $$F_L = \left[\frac{n2-n1}{n1} * \left(\frac{1}{R1} - \frac{1}{R2}\right) + \frac{(n2-n1)^2*d}{n1*n2*R1*R2}\right].$$

Here, $R_1$ is for example the radius of the first optical surface which is produced in reality and $R_2$ is the radius of the calculated base surface (the additive height z, which supplies the additional focal power, can also be added to the radius $R_1$ or can be split over both radii $R_1$ and $R_2$; the formulae then have to be modified accordingly).

The height profile $z_L$ for the calculated base surface with the radius $R_2$ of the spherical lens emerges as $z_L(x, y)=R_2-\sqrt{R_2^2-x^2-y^2}$, and, with $r=\sqrt{x^2+y^2}$, the data of the base surface in polar coordinates emerge as $z_L(r)=R-\sqrt{R^2-r^2}$.

Thus, for the case of a spherical base surface, the following applies:

$$z_G(r,phi)=(R-\sqrt{R^2-r^2})+z_{max}(r,phi)*w(phi).$$

To the extent that non-spherical base surfaces underlie the lens, the known polynomials for describing non-spherical surfaces are used for determining the optical surfaces and/or the base surface. The additional focal power here in case a) is generated by an additive term z(r, phi) as material height, which, for example, is added to the optical base surface with the radius $R_2$ or else subtracted therefrom. Analogous considerations also apply to aspherical and free-form surfaces which cannot be described by a simple specification of a radius.

The radial polynomial for the maximum height component as a function of the radius r for focal power $z_{max}(r)$, which embodies the maximum diopter number to be obtained, is:

$$z_{max}(r) = \sum_{j=2}^{N} c_j * r^j,$$

where r is the radial height and $c_i$ is a coefficient set of the radial polynomial.

$$w(phi) = \frac{phi}{2\pi}$$

is the angle-dependent, linearly normalized component, with phi as azimuth angle on the base surface of the base system (carrier lens).

The additive term z(r, phi), which is added to the base surface of the lens, emerges from $$z(r, phi) = z_{max}(r) * w(phi) = \sum_{j=2}^{N} c_j * r^j * \frac{phi}{2\pi}.$$

Thus, in the simplest case, it is already sufficient to realize the additional radial focal power distribution as a product of the normalized azimuth angle with the maximum diopter number to be obtained.

For the radial polynomial $z_{max}(r)$, the approach $$z_{max}(r) = \sum_{j=1}^{N} c_j * r^{2*j}$$

can also be used in an analogous manner.

For the simplest case of the radial polynomial $z_{max}(r) = c_1 * r^2$, with $c_1$ as coefficient in front of the quadratic term, the equation for the additive term thus reads $$z(r, phi) = z_{max}(r) * w(phi) = c_1 * r^2 * \frac{phi}{2\pi}.$$

The procedure described above represents a linear "helical increase". In this form, the imaging quality is good with approximately no change over the whole diopter range.

However, it is often desirable to prefer specific diopter regions such as e.g. the zero diopter position. To this end, it is necessary to depart from the linear dependence of the z-height on the angle.

In general, the angle-dependent component can be described by the formula $$w(phi) = \sum_{i=1}^{M} I_i * \exp[-a_i * (phi - w_i)^2],$$

where $w_i$ are the peak positions (between 0 and $2\pi$), $I_i$ are the peak intensities and $a_i > 0$ are the damping coefficients for the respective peak positions.

By way of example, for M=1; $I_1 = 1$ and $w_i = 2\pi$, the function $$z(r, phi) = z_{max}(r) * w(phi) = \sum_{j=2}^{N} c_j * r^j * \exp[-a_1 * (phi - 2\pi)^2]$$

with $a_1 = 0.25$ allows a preference for the zero diopter region to be implemented. The small increase between phi=0 and phi=2 causes a small addition of focal power in this angular range and hence a larger surface component for the zero diopter distance.

In the context of optimizing the lens with the extended range of focus, further advantages can be obtained by virtue of further degrees of freedom being available during the design. By way of example, this is brought about if the radial function $z_{max}(r)$ likewise obtains an azimuth-dependent set of coefficients and hence the radial polynomial $z_{max}(r, phi)$ is determined as $$z_{max}(r, phi) = \sum_{j=2}^{N} c_j(phi) * r^j \text{ or } z_{max}(r, phi) = \sum_{j=1}^{N} c_j(phi) * r^{2*j}.$$

From this, the additive term z(r, phi) emerges in general as e.g.

$$z(r, phi) =$$

$$z_{max}(r, phi) * w(phi) = \sum_{j=2}^{N} c_j(phi) * r^j * \sum_{i=1}^{M} I_i * \exp[-a_i * (phi - w_i)^2].$$

Hence, it is possible to specify further variants from the general formula $$w(phi) = \sum_{i=1}^{M} I_i * \exp[-a_i * (phi - w_i)^2]$$

for the angle term w(phi), by means of which it is possible to control the "effective period" of the individual azimuth ranges.

The explanations above were based upon an additive term which is refractive and which is added to one of the optical surfaces of the base system. The addition term can naturally also be available in a diffractive form, i.e. a diffractive optical element (DOE) with a spiral phase function is applied to the spherical carrier surface of the base system (case b)). This phase function is designed in a completely analogous fashion to the refractive approach. Blaze gratings, sinusoidal gratings and binary gratings are particularly suitable. In a radial and angle-dependent manner, the grating frequency changes continuously in a spiral manner from a value zero to a maximum value corresponding to the maximum focal power.

$$Phase_{max}(r) = \sum_{j=2}^{N} k_j * r^j \text{ or } Phase_{max}(r) = \sum_{j=1}^{M} k_j * r^{2*j},$$

with $k_1$ as coefficient of the quadratic term, the maximum focal power, $$F_{Smax\ diffractive} = 2k_1 \frac{\lambda}{wl},$$

emerges and the angle-dependent term, $F_{Sdiffractive}$ (phi), emerges as $$F_{S\ diffractive} = 2k_1 \frac{\lambda}{wl} * w(phi),$$

where wl is the design wavelength of the diffractive optical element and $\lambda$ is an application wavelength.

The overall focal power of the lens emerges from a comparatively strong refractive basic focal power of the monofocal base system and from a relatively small focal power component of the additional focal power generated by diffraction:

$$F_{G\ diffractive} = F_L + F_{S\ diffractive} = F_L + 2k_1 \frac{\lambda}{wl} * w(phi).$$

Thus, as a result of the diffractive component, a relatively only small color aberration is created and the lens with the extended range of focus is also suitable for white light.

However, the addition term can also be realized by producing a spiral refractive index gradient (case c)). DE 10 2009 033 984 A1 describes how inhomogeneous optical properties can be generated in an optical material. In a development of the method described therein, it is also possible to realize a spiral refractive index profile. The properties and the design of the refractive index gradient in this case are brought about in a completely analogous fashion to the refractive approach.

The overall focal power $F_G$ emerges from the basic focal power $F_L$ of the monofocal base system plus the additional focal power $F_S$ which is provided by the spiral focal power increase.

$$F_G = F_L + F_S(r, phi)$$
$$= \frac{1}{f_L} + \frac{1}{f_S(r, phi)},$$

where $f_L$ is the focal length of the base system and $f_S$ is the focal length of the spiral additional focal power caused by the refractive index gradient. The additional focal power $F_S$(r, phi) is proportional to the refractive index difference $\Delta n$(r, phi) in accordance with the formula $$\Delta n(r,phi) = \Delta n_{max}(r) * w(phi).$$

or $$\Delta n(r,phi) = \Delta n_{max}(r,phi) * w(phi).$$

The refractive index difference $\Delta n$(r, phi) increases continuously from 0 (at r=0 and phi=0) to the maximum refractive index increase $\Delta n_{max}$ (at r=D/2 and phi=2$\pi$), where the function w(phi) can prescribe the above-described linear or general profile.

Here, $\Delta n_{max}$ can be both positive and negative compared to the base refractive index $n_2$ of the lens.

The methods described above are employed to impress the spiral focal power distribution $F_S$(r, phi) upon and/or into an eye lens, a phakic intraocular lens or an aphakic intraocular lens.

The invention furthermore relates to a lens system with an extended range of focus, which has a lens according to the invention with an extended range of focus in the beam path as an imaging element.

It is understood that the features which were explained above and are yet to be explained below can be employed not only in the specified combinations, but also in other combinations or on their own, without departing from the scope of the present invention.

The invention will be described below on the basis of figures, in which:

FIG. 1 shows a lens with an extended range of focus with the spiral focal power profile in a top view as step image of the focal power change. In principle, the illustration applies to the cases:

a) "Adding" a spiral height profile to one of the optical surfaces of the lens as per step 1, which is the base surface.
b) "Adding" a spiral diffractive structure to one of the optical surfaces of the lens as per step 1, which is the base surface.
c) "Adding" a spiral refractive index profile in the material of the lens.

In the example, the lens has conventional spherical optical surfaces and a lens thickness, which form a base system which is designed with a "base refractive index" of 1.5995 for 0 dpt correction. The additional spiral focal power distribution is realized by a spiral refractive index gradient and begins at phi=0 with the refractive index of 1.5995. Depending on radius and angle, the refractive index increases continuously in a spiral fashion and has, for example, a refractive index of 1.61366 at phi=n and r=D/2. This corresponds to a focal power of 1.0 dpt. The refractive index continues to increase continuously and has a refractive index of 1.64615 at phi=2π and r=D/2, corresponding to a focal power of 3.5 dpt. The difference in refractive index between phi=0 and phi=2π is 0.04665. This corresponds to a usable continuous range of focus between 0 dpt and 3.5 dpt.

Figure 1:
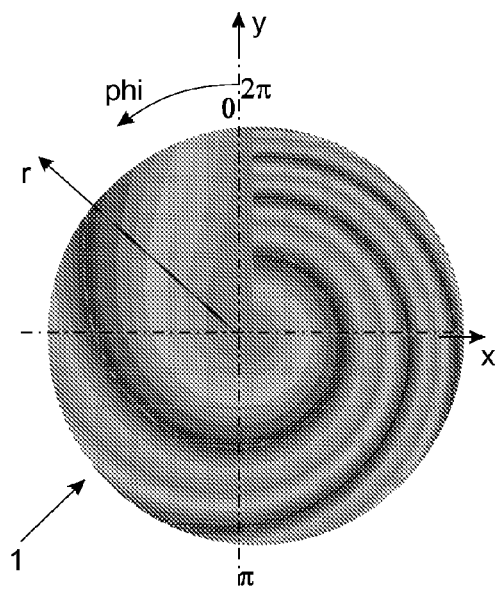
FIG. 1 shows a top view of a lens with an extended range of focus in a grayscale image with the spiral focal power profile.
Figure 2:
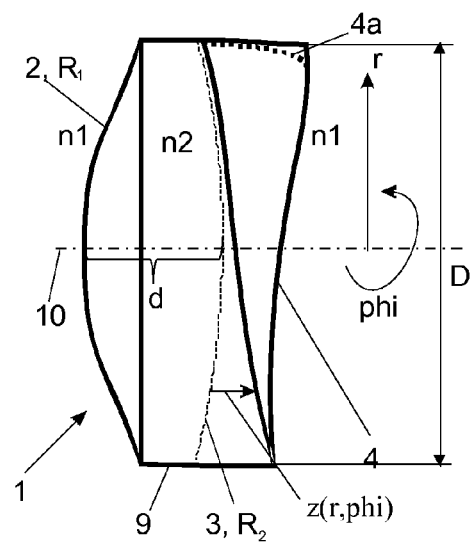
FIG. 2 shows a side view of a lens with an extended range of focus with a depiction of the spiral refractive component.

FIG. 2 shows a side view of a lens with an extended range of focus with a depiction of the spiral refractive component. The lens 1 is initially determined by its base system with the radius $R_1$ of the first optical surface 2 and the radius $R_2$ for the calculated base surface 3, and also by the lens thickness d and the refractive index $n_2$. These parameters are provided for an envisaged basic magnification. An additional material thickness z is "added" to the calculated shape of the base surface 3 with the radius $R_2$, with the additional material thickness being z=0 mm at phi=0, then increasing continuously and having its maximum value in the millimeter range at phi=2π. In practice, the maximum value will lie slightly in front of the azimuth angle phi=2π in order to realize a continuous, albeit very steep, transition back to the value zero at phi=0, as indicated by the dashed curve denoted by 4a.

Parameters for a lens are specified as an example:
$R_1$=−15.1411 mm radius to be produced
$R_2$=22.3164 mm calculated radius
d=0.8 mm
$n_1$=1 (refractive index outside of the lens)
$n_2$=1.56 (refractive index of the lens medium)
Hence, from the formula $$f = \frac{1}{\left[\frac{n2-n1}{n1} * \left(\frac{1}{R1} - \frac{1}{R2}\right) + \frac{(n2-n1)^2 * d}{n1 * n2 * R1 * R2}\right]},$$

the focal length of the "base lens" emerges as 16.233 mm.

A linear helical increase in accordance with the formula $$z(r, phi) = z_{max}(r) * w(phi)$$
$$= c_1 * r^2 * \frac{phi}{2\pi}$$

as a continuous, spiral height profile with a linear extent is added to the calculated base surface with the radius $R_2$=22.3164 mm.

With $c_1$=−0.013, a spiral addition which increases the focal length in air up to 20.57 mm, corresponding to 3.5 dpt, is obtained.

Figure 3:
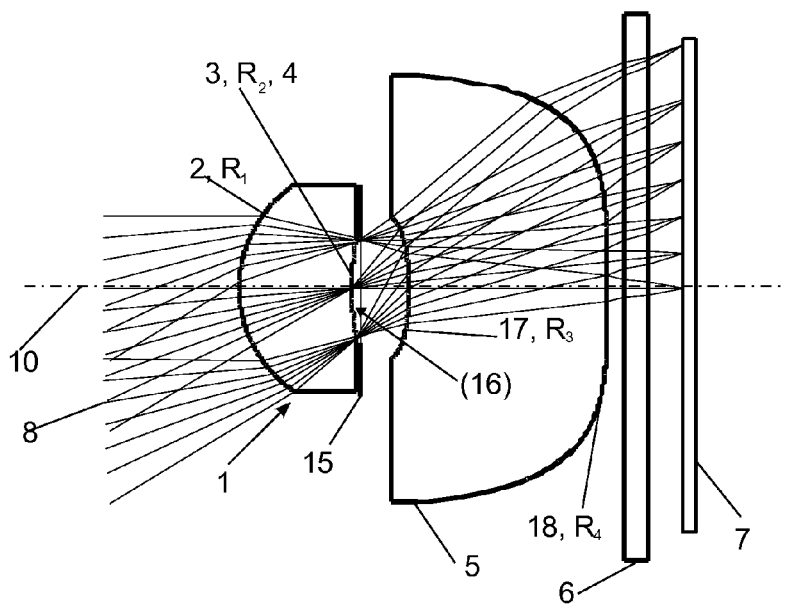
FIG. 3 shows an optical system of a camera with a lens with the extended range of focus.

FIG. 3 shows an optical system of a camera with a lens 1 according to the invention, which has the extended range of focus. The optical system consists of the extended focus lens 1 and this is followed in the light propagation direction by an aspherical lens 5 with the optical surfaces 17 and 18; this is then followed by a filter 6 and a sensor 7. On the object side, the extended focus lens 1 has a first optical surface 2. The second optical surface 4 with the spiral design is arranged on the image side.

A lens system of a cellular telephone with a focal length of 5.61 mm is shown as an example. In accordance with the formula for the spiral, linear helical increase $$z(r, phi) = c_1 * r^2 * \frac{phi}{2\pi},$$

the shape of the spiral optical surface 4 over the calculated base surface 3 emerges, analogously to as described in relation to FIG. 2, using the parameters $c_1$=−0.01; phi=0 to 2π (azimuth angle); r=radial height between 0 and D/2. The base surface 3 is concave and spherical in the example, with the radius $R_2$=5.21369 mm.

The optical surfaces 17 and 18 of the lens 5 and the first optical surface 2 of the extended focus lens 1 are rotationally aspherical. The parameters of the lens system are: focal length f=5.61 mm; design length 6.8 mm; aperture 1:2.8.
Lens 1:
Thickness 1.738 mm; material=Zeonex
First optical surface 2: $R_1$=1.7668 mm
Asphere coefficients:
K=−0.162288
A=0.472171E-04
B=0.225901E-02
C=−0.179019E-03
D=−0.290228E-03
E=0.131193E-03
Second Optical Surface 4

The calculated radius of the base surface 3 for the basic focal power of the lens $F_L$ is $R_2$=5.21369 mm (concave, spherical). The basic focal length of the lens is 330 mm, corresponding to an additional focal power of at most 3.0 dpt.

The surface shape of the base surface can be described by the formula $z_L(r)=R_2-\text{sign}(R_2)\sqrt{R_2^2-r^2}$. The additive height emerges from $$z(r, phi) = z_{max}(r) * w(phi)$$
$$= c_1 * r^2 * \frac{phi}{2\pi},$$

with the coefficient of the polynomial $c_1$=−0.01.

The additive height should be added to each surface point of the base surface such that the overall height profile of the second optical surface is determined by the following formula:

$$z_G(r, phi) = \left(R_2 - \text{sign}(R_2)\sqrt{R_2^2 - r^2}\right) + c_1 * r^2 * \frac{phi}{2\pi}.$$

Lens 5:
Thickness 2.703 mm; material=polycarbonate
Surface 17: R=−3.85282 mm
Asphere coefficients:
K=16.027906
A=−0.687655E-01
B=0.676838E-01
C=−0.101439E+00
D=0.900331E-02
E=0.345714E-01
F=−0.101087E-01
G=0.950453E-16
H=0.443668E-17
J=0.105965E-19

Surface 18: $R_4$=413.75417 mm
Asphere coefficients:
K=−0.238656e57
A=−0.200963E-01
B=0.297531E-02
C=−0.110276E-02
D=0.209745E-03
E=−0.935430E-05
F=−0.430237E-05
G=0.434653E-06
H=0.475646E-07
J=−0.612564E-08
Distance lens 1 to lens 5: 0.571 mm
Distance lens 5 to filter 6: 0.4 mm
Distance filter to image plane of detector 7: 0.4 mm
Thickness of filter 6: 0.4 mm The optical system has a design length of 6.8 mm. The aperture is 1:2.8. The lens system supplies a sufficiently good image quality, obtained without refocusing, for an object distance from 330 mm to infinity. It is advantageous that the spiral optical second surface is situated on the rear side of the front lens, wherein the residual surface of the rear side, which is not filled by the spiral optical surface, forms a stop 15.

A further exemplary embodiment describes a lens system for a camera with a focal length of f=6.1 mm, having a design length of 6.8 mm and an aperture of 1:2.8. The illustration corresponds to the one shown in FIG. 3. The lens 1 with the extended range of focus has a first optical surface 2 on the object side. The second optical surface 4 thereof corresponds in terms of its surface shape to the calculated base surface 3 and carries the diffractive optical element 16, which supplies the spiral focal power profile in addition to the focal power of the base system.

All optical surfaces 3, 4, 17 and 18 of the lenses 1 and 5 have a rotationally aspherical basic shape.
Lens 1: lens thickness=1.59 mm, material=Zeonex
Optical surface 2: $R_1$=1.77985
Asphere coefficients:
K=0.113528
A=−0.369422E-02
B=0.497838E-05
C=−0.526491E-03
Optical surface 4 (corresponds to calculated surface 3):
$R_2$=4.43773
Asphere coefficients:
K=20.010847
A=−0.165668E-01
B=0.598703E-01
C=−0.239849E+00
D=0.363395E+00
E=−0.231421E+00

The diffractive optical element 16 has the coefficient of the spiral polynomial $k_1$=−2.1350E-03.
The additional spiral focal power component is calculated by $$F_{Sdiffractive} = 2k_1 * \frac{phi}{2\pi} * \frac{\lambda}{wl}$$

and the overall focal power emerges as $$F_{Gdiffractive} = F_L + F_{Sdiffractive}$$

$$= F_L + 2k_1 * \frac{phi}{2\pi} * \frac{\lambda}{wl}.$$

The lens 5 has a thickness of 2.98 mm, material=polycarbonate
Surface 17: $R_3$=−4.60229 mm
Asphere coefficients:
K=12.980316
A=−0.289939E-01
B=−0.193341E-01
C=0.430879E-01
D=−0.575934E-01
E=0.345714E-01
F=−0.101087E-01
Surface 18: $R_4$=−51.75016 mm
Asphere coefficients:
K=−0.238656e57
A=−0.128992E-01
B=0.257544E-02
C=−0.116486E-02
D=0.176791E-03
E=−0.381907E-06
F=−0.294503E-05
G=0.250155E-06
H=0.303670E-08
J=−0.768736E-09

The distance between lens 1 and lens 5 is 1.05 mm; the distance between lens 5 and filter 6 is 0.4 mm and the distance from filter 6 to the image plane of detector 7 is 0.4 mm, with the filter thickness likewise being 0.4 mm.

The lens system supplies a simultaneous range of focus from 330 mm to infinity.

Here, in particular, the expedient selection of the coefficient c in front of the quadratic term supports the achromatization of the lens system.

Figure 4:
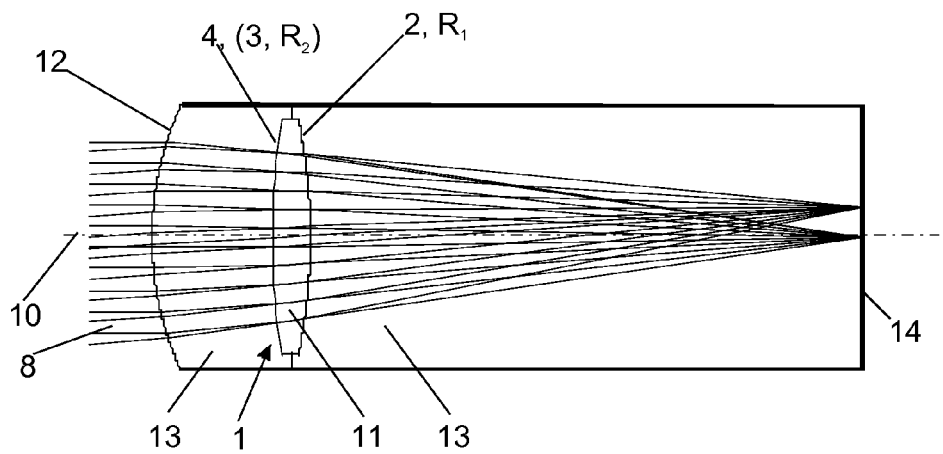
FIG. 4 shows a schematic depiction of an intraocular lens in the eye.

FIG. 4 shows a schematic illustration of an intraocular lens 11, which is implanted into the eye as extended focus lens 1. In the example, it replaces the natural lens of the eye and is situated in the light path between the cornea 12 and the retina 14 in the aqueous humor 13.

The intraocular lens 11 has a spherical first optical surface 2 and the spiral second optical surface 4. By way of example, the intraocular lens 11 with the extended range of focus has the following parameters for the base system:
$R_1$=−15.1411 mm (produced first optical surface 2)
$R_2$=22.3164 mm (calculated base surface 3)
Lens thickness d=0.8 mm
Refractive index outside of the lens $n_1$=1.33
Refractive index of the lens medium $n_2$=1.56
Using the formula $$f = \frac{1}{\left[\frac{n2-n1}{n1} * \left(\frac{1}{R1} - \frac{1}{R2}\right) + \frac{(n2-n1)^2 * d}{n1 * n2 * R1 * R2}\right]},$$

the base focal length f=53.97 mm emerges for the base system of the intraocular lens 11 in the aqueous humor 13.

The additional focal power emerges from the additive height on the base surface using the formula $$z(r, phi) = c_1 * r^2 * \frac{phi}{2\pi},$$

where $c_1$=−0.013.

The "added" spiral surface would extend the value of the base focal length from 16.233 mm to 17.2 mm, corresponding to 3.5 dpt. Accordingly, the extended focus lens supplies a variance in the diopter range between 0 dpt and 3.5 dpt.

Figure 5:
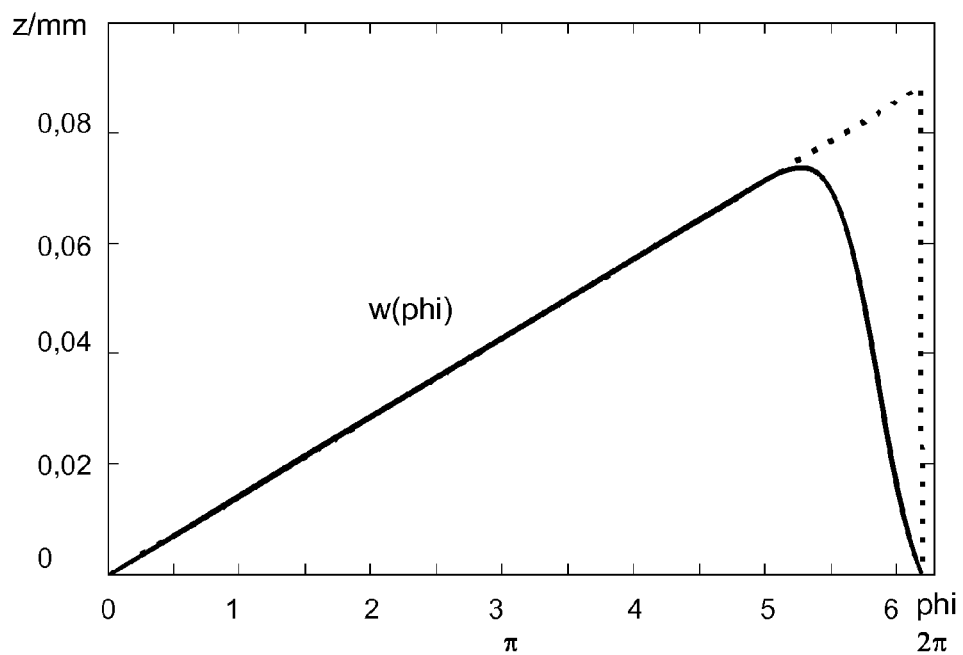
FIG. 5 shows an azimuth profile of the spiral component of the focal power profile, modulated thereon, with mainly a linear increase.

FIG. 5 shows the azimuth profile of the spiral component of the focal power profile modulated onto the base surface with a predominantly linear increase corresponding to the formula $$z(r, phi) = z_{max}(r) * w(phi)$$
$$= c_1 * r^2 * \frac{phi}{2\pi}$$

for the additive component of the focal power.

So that this can be produced in an improved fashion and in order to avoid sharp transitions, the curve profile is smoothed near $2\pi$.

Figure 6:
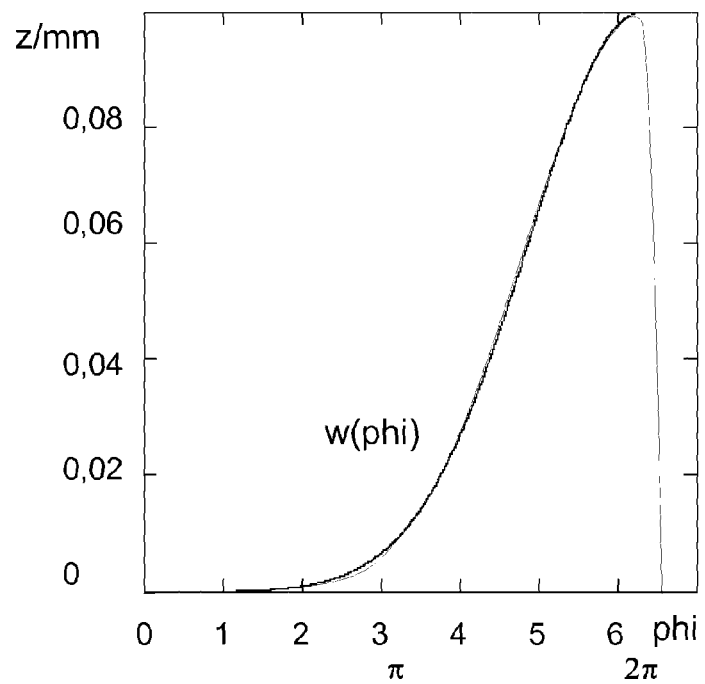
FIG. 6 shows an azimuth profile of the spiral component of the focal power profile, modulated thereon, with preference for the zero diopter region.

FIG. 6 shows the azimuth profile of the spiral component of the focal power profile modulated thereon, with preference for the zero diopter region. In practice, it is often desirable to prefer specific diopter regions such as, for example, the zero diopter position. To this end, it is necessary to depart from the linear dependence of the z-height on the angle. By way of example, by means of the function $$z(r, phi) = z_{max}(r) * w(phi)$$
$$= \sum_{j=1}^{N} c_j * r^{2*j} * \exp[-a*(phi-2\pi)^2]$$

with a=0.25, it is possible to realize a preference for the zero diopter region. The angle-dependent component $w(phi) = \exp[-a*(phi-2\pi)^2]$ is depicted in FIG. 6. The small increase between phi=0 and phi=2 causes a small addition of focal power in this angular range and hence a larger surface component for the zero diopter distance.

Figure 7:
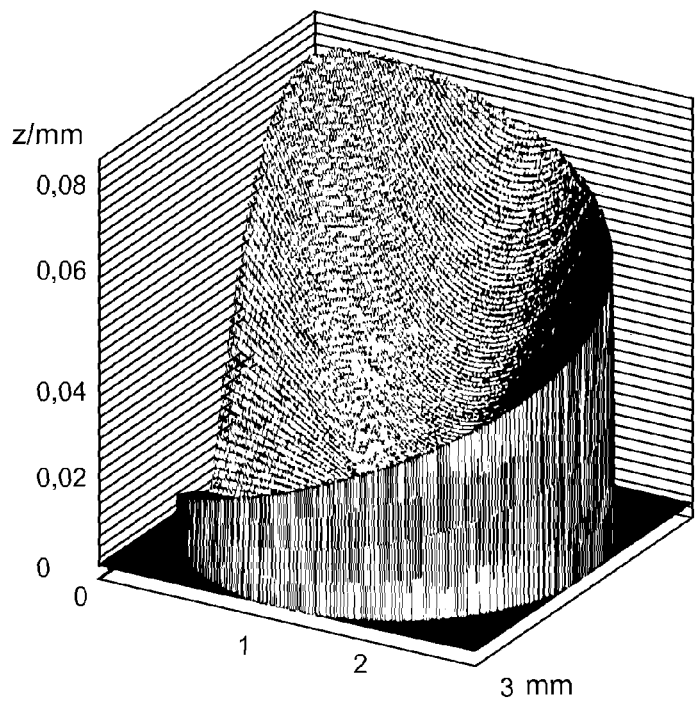
FIG. 7 shows a much exaggerated depiction of an extended focus lens surface with a spiral height profile modulated thereon.

FIG. 7 shows an exaggerated illustration of the additive height profile with the spiral extent in accordance with FIG. 2. The spiral optical surface 4 is created by virtue of the fact that the azimuth-dependent polynomial function is added to the spherical base surface 3. What is illustrated is the height z over the diameter of the lens surface, which is being purely added to the spherical base surface 3 as per FIG. 2.

Figure 8:
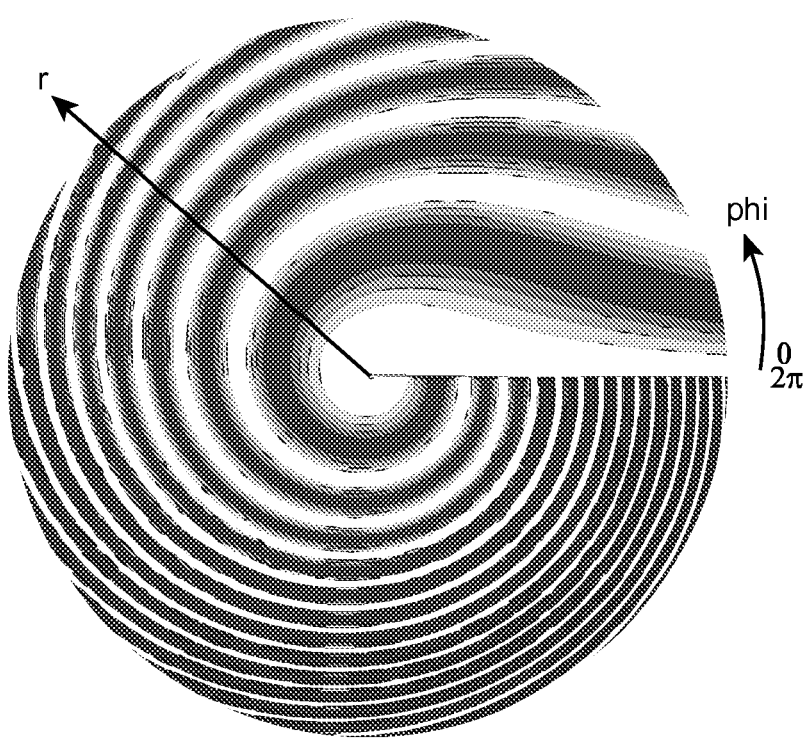
FIG. 8 shows a top view of a lens with an extended range of focus with a depiction of the spiral diffractive component.

FIG. 8 shows a lens with an extended range of focus, which was calculated according to the diffractive approach in accordance with the variant b), in a top view, wherein all that is visible is the spiral diffractive component. In this case of generating the spiral focal power distribution of the lens by means of the diffractive approach, the phase function is:

$$\text{Phase}(r, phi) = \text{Phase}_{max}(r) * w(phi)$$
$$= \left(\sum_{j=2}^{N} k_j * r^j\right) * \left(\sum_{i=1}^{M} I_i * \exp[-a_i*(phi-w_i)^2]\right)$$

Using $$t = \sum_{j=2}^{N} k_j * r^j * \sum_{i=1}^{M} I_i * \exp[-a_i*(phi-w_i)^2],$$

the profile(r, phi) emerges as $$\text{Profile}(r, phi) = \left(\frac{t}{wl} - \text{floor}\left(\frac{t}{wl}\right)\right) * h$$

$$\text{Profile}(r, phi) =$$

$$\left(\frac{\sum_{j=2}^{N} k_j * r^j * \sum_{i=1}^{M} I_i * \exp[-a_i*(phi-w_i)^2]}{wl} - \text{floor}\left(\frac{\sum_{j=2}^{N} k_j * r^j * \sum_{i=1}^{M} I_i * \exp[-a_i*(phi-w_i)^2]}{wl}\right)\right) * h,$$

where $k_j$ is a coefficient of the diffractive polynomial; r is the radius (radial height); $I_i$ are intensities; $a_i$ are damping coefficients; wl is the design wavelength of the DOE and h is the profile depth.

In the special linear case, the following applies:

$$\text{Phase}(r, phi) = \text{Phase}_{max}(r) * w(phi)$$
$$= k_1 * r^2 * \frac{phi}{2\pi}.$$

Using $$t = k_1 * r^2 * \frac{phi}{2\pi},$$

the following emerges:

$$\text{Profile}(r, phi) =$$

$$\left(\frac{t}{wl} - \text{floor}\left(\frac{t}{wl}\right)\right) * h = \left(\frac{k_1 * r^2 * phi}{wl * 2\pi} - \text{floor}\left(\frac{k_1 * r^2 * phi}{wl * 2\pi}\right)\right) * h.$$

Example data are: coefficient of the diffractive polynomial $k_1 = 0.0025$, the height r in the range from 0 to 3 mm, the azimuth angle phi in the range from 0 to $2\pi$, design wavelength of the DOE wl=550 nm, profile depth h=0.001 mm.

Figure 9:
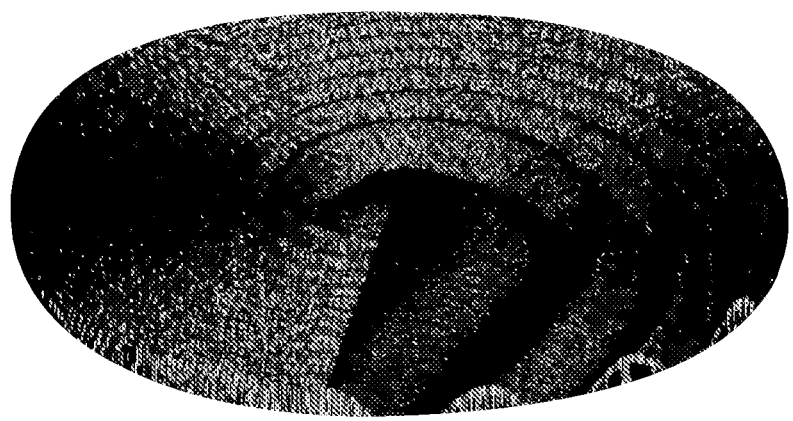
FIG. 9 shows a perspective top view of a lens with an extended range of focus with a depiction of the spiral diffractive component.

FIG. 9 shows the lens with the extended range of focus in a perspective top view on the diameter of the lens with depiction of the spiral diffractive component.

Figure 10:
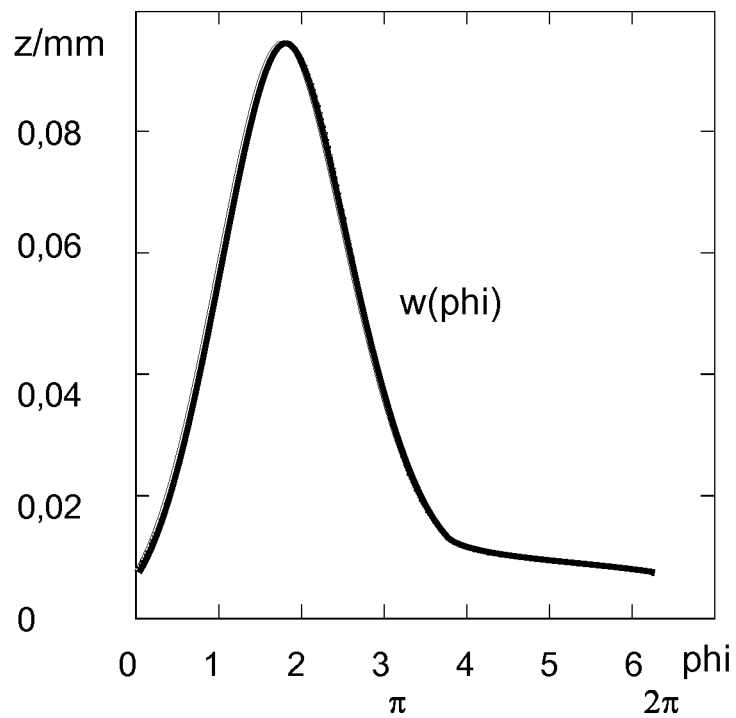
FIG. 10 shows an azimuth profile of the additional focal power with extended range for the strong diopter position.

A profile of the angle-dependent factor w(phi) is depicted in FIG. 10.

Using the following modified formula for the angular dependence:

$$w(phi) = I_1 * \exp[-a_1*(phi-w_1)^2] + I_2 * \exp[-a_2*(phi-w_2)^2],$$

where $w_1, w_2$: peak positions (between 0 and 2*pi), $I_1, I_2$: peak intensities, and $a_1, a_2$: damping coefficients for the two peaks, a profile for the azimuth dependence, in which an extended range is reserved for the strongest diopter position (approximately 3 dpt), emerges using, for example, the values:

$I_1=0.9$; $I_2=0.1$; $a_1=0.8$; $a_2=0.1$; $w_1=1.8$; $w_2=4.5$.

Figure 11:
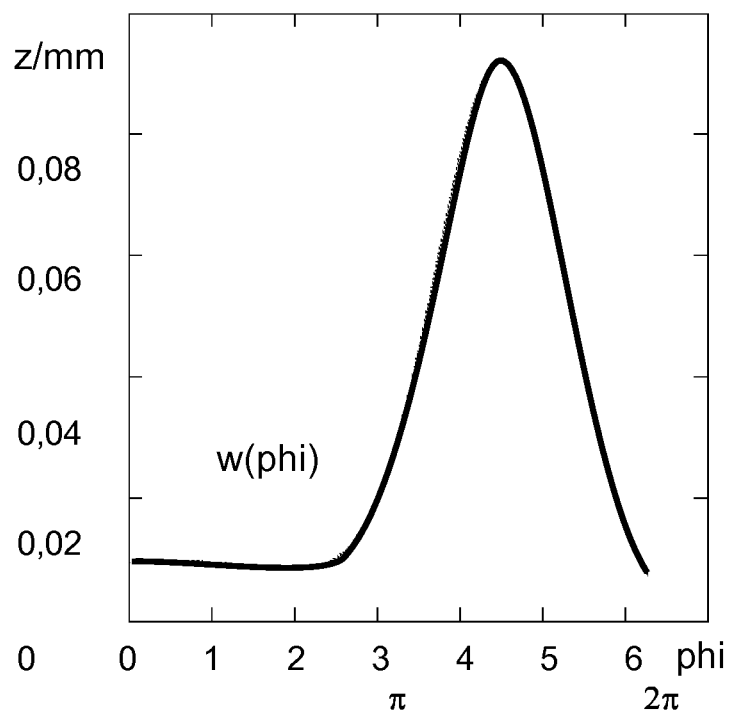
FIG. 11 shows an azimuth profile of the additional focal power with preference for the zero diopter region.

Using the values $I_1=0.9$; $I_2=0.1$; $a_1=0.8$; $a_2=0.1$; $w_1=4.5$; $w_2=0.5$, the zero diopter region is clearly preferred by the formula $$w(phi) = I_1 * \exp[-a_1*(phi-w_1)^2] + I_2 * \exp[-a_2*(phi-w_2)^2],$$

which is illustrated in FIG. 11.

LIST OF REFERENCE SIGNS

1 Lens
2 Manufactured first optical surface (spherical, aspherical, radially symmetric, free-form surface)
3 Calculated base surface (spherical, aspherical, radially symmetric, free-form surface)
4 Manufactured second optical surface (spherical, aspherical, radially symmetric, free-form surface, spiral surface)
5 Aspherical lens
6 Filter
7 Sensor
8 Bundle of light
9 Lens edge
10 Optical axis
11 Intraocular lens
12 Cornea
13 Aqueous humor
14 Retina
15 Stop
16 Spiral diffractive optical element (DOE)
17 Optical surface
18 Optical surface
$F_G$ Overall focal power of the lens
$F_L$ Focal power of the base system of the lens
$F_S(r, phi)$ Focal power which is added to the focal power of the base system by the spiral component
$F_{Smax}$ Maximum focal power
$f_L$ Focal length of the base system
$f_S(r, phi)$ Focal length of the spiral additional focal power
N, M Final values
i, j Counters
$c_j, c_1, c_2$ Polynomial coefficients for the refractive case
$k_j, k_1, k_2$ Polynomial coefficients for the diffractive case
$z_{max}(r)$ Maximum height, dependent on the radius
$z_{max}(r, phi)$ Maximum height, dependent on the radius and azimuth angle
$z(r, phi)$ Additive height on the base surface
$z_L(r)$ Height profile of the calculated base surface
$z_G(r, phi)$ Height profile of the manufactured optical surface
w(phi) Angle-dependent component of the focal power profile
$w_i, w_1, w_2$ Peak positions of the angular distribution function
$a_i, a_1, a_2$ Damping coefficients for the respective peak positions
$I_i, I_1, I_2$ Intensity values of the individual peaks
D Lens diameter
r Radius (radial height)
phi Azimuth angle
$R_1$ Radius of the first optical surface
$R_2$ Radius of the optical base surface
$n_1$ Refractive index of the surrounding medium
$n_2$ Refractive index of the lens
d Lens thickness
h Profile depth of the diffractive element
λ Application wavelength
wl Design wavelength of the diffractive element
t Calculation variable
floor(t) Integer component
$Phase_{max}(r, phi)$ Maximum value of the grating frequency, which corresponds to the maximum focal power
Phase(r, phi) Phase function
Profile(r, phi) Phase function reduced to the height h
x, y Cartesian coordinates

The invention claimed is:

1. A lens with an extended range of focus, wherein the lens consists of a solid, transparent material and has two manufactured optical surfaces, wherein the lens has a focal power distribution $F_G$, characterized in that
the focal power distribution $F_G$ of the lens, in relation to a plane perpendicular to the optical axis, changes as a function of the radial height r and of the azimuth angle phi of the aperture between a base value of the focal power $F_L$ not equal to zero and a maximum value $F_{Smax}$ and hence results in the focal power distribution $$F_G(r,phi)=F_L+F_S(r,phi),$$

with a spiral focal power component $$F_S(r,phi)=F_{Smax}(r,phi)*w(phi),$$

where $F_{Smax}(r)$ depends nonlinearly on the radius and w(phi) is a factor for the focal power component with the spiral profile, which, in general, is described by the formula $$w(phi) = \sum_{i=1}^{N} I_i \exp[-a_i(phi-w_i)^2],$$

and $w_i$ are the peak positions in the angular distribution function; $I_i$ are intensity values of the individual peaks; $a_i>0$ are damping coefficients for the respective peak positions and i is a counter and M≥i is a final value.

2. A lens with an extended range of focus, wherein the lens consists of a solid, transparent material and has two manufactured optical surfaces, wherein the lens has a focal power distribution $F_G$, characterized in that
the focal power distribution $F_G$ of the lens, in relation to a plane perpendicular to the optical axis, changes as a function of the radial height r and of the azimuth angle phi of the aperture between a base value of the focal power $F_L$ not equal to zero and a maximum value $F_{Smax}$ and hence results in the focal power distribution $$F_G(r,phi)=F_L+F_S(r,phi),$$

with a spiral focal power component $$F_S(r,phi)=F_{Smax}(r,phi)*w(phi),$$

where $F_{Smax}(r)$ depends nonlinearly on the radius and w(phi) is a factor for the focal power component with the spiral profile, which is described as a linear profile by the formula $$w(phi) = \frac{phi}{2\pi}.$$

3. The lens as claimed in claim 1 or as claimed in claim 2, characterized in that the maximum focal power $F_{Smax}(r)$ depends nonlinearly on the radius and is described by the polynomial formulae $$F_{Smax}(r) = \sum_{j=2}^{N} c_j * r^j \text{ or } F_{Smax}(r) = \sum_{j=1}^{N} c_j * r^{2*j},$$

with the polynomial coefficients $c_j$ for a refractive focal power and $$F_{Smax}(r) = \sum_{j=2}^{N} k_j * r^j \text{ or } F_{Smax}(r) = \sum_{j=1}^{N} k_j * r^{2*j},$$

with the polynomial coefficient $k_j$ for a diffractive focal power, where j is a counter and $N \geq j$ is a final value.

4. The lens as claimed in claim 1 or as claimed in claim 2, characterized in that the maximum focal power $F_{Smax}(r, phi)$ depends nonlinearly on the radius and is dependent on the azimuth angle phi of the aperture is described by the polynomial formulae $$F_{Smax}(r, phi) = \sum_{j=2}^{N} c_j(phi) * r^j \text{ or } F_{Smax}(r, phi) = \sum_{j=1}^{N} c_j(phi) * r^{2*j},$$

with the polynomial coefficients $c_j$ for a refractive focal power and $$F_{Smax}(r, phi) = \sum_{j=2}^{N} k_j(phi) * r^j \text{ or } F_{Smax}(r, phi) = \sum_{j=1}^{N} k_j(phi) * r^{2*j},$$

with the polynomial coefficient $k_j$ for a diffractive focal power, where j is a counter and $N \geq j$ is a final value.

5. The lens as claimed in claim 3, characterized in that the focal power distribution $F_G(r, phi)$ of the lens emerges from a height profile $z_G(r, phi)$ of a second optical surface to be manufactured, which emerges from adding the height profile $z_L(r)$ of a calculated base surface and a height profile $z(r, phi)$, where $$F_G(r, phi) = F_L + F_S(r, phi)$$
$$= z_G(r, phi)$$
$$= z_L(r) + z(r, phi)$$

applies, where the additive height $z(r, phi)$ changes nonlinearly dependent on the radius, starting from zero to a maximum value $z_{max}(r)$ which supplies the maximum focal power $F_{Smax}(r)$, and emerges as a function $$z(r, phi) = z_{max}(r) * w(phi),$$

with $$z_{max}(r) = \sum_{j=2}^{N} c_j * r^j \text{ or } z_{max}(r) = \sum_{j=1}^{N} c_j * r^{2*j},$$

where the radius r changes continuously between 0 and D/2 and the azimuth angle phi of the aperture changes continuously between 0 and $2\pi$, as a result of which the optical surface to be manufactured is described by the spiral height profile.

6. The lens as claimed in claim 4, characterized in that the focal power distribution $F_G(r, phi)$ of the lens emerges from a height profile $z_G(r, phi)$ of the second optical surface to be manufactured, which emerges from adding the height profile $z_L(r)$ of a calculated base surface and a height profile $z(r, phi)$, where $$F_G(r, phi) = F_L + F_S(r, phi)$$
$$= z_G(r, phi)$$
$$= z_L(r) + z(r, phi)$$

applies, where the additive height $z(r, phi)$ changes nonlinearly dependent on the radius and dependent on the azimuth angle phi of the aperture, starting from zero to a maximum value $z_{max}(r, phi)$ which supplies the maximum focal power $F_{Smax}(r, phi)$, and emerges as a function $$z(r, phi) = z_{max}(r, phi) * w(phi),$$

with $$z_{max}(r, phi) = \sum_{j=2}^{N} c_j(phi) * r^j \text{ or } z_{max}(r, phi) = \sum_{j=1}^{N} c_j(phi) * r^{2*j},$$

where the radius r changes continuously between 0 and D/2 and the azimuth angle phi of the aperture changes continuously between 0 and $2\pi$, as a result of which the optical surface to be manufactured is described by the spiral height profile.

7. The lens as claimed in claim 3, characterized in that the focal power component with the spiral profile $F_S(r, phi)$ emerges from the effect of an optical grating applied to a manufactured second optical surface with the focal power $F_L$, where $$F_G(r, phi) = F_L + F_S(r, phi) = F_L + \text{Phase}(r, phi)$$

applies, and the frequency of the optical grating changes nonlinearly dependent on the radius, starting from a base value zero to a maximum value $\text{Phase}_{max}$ which supplies the maximum focal power $F_{Smax}$, wherein the following applies to the spiral focal power profile:

$$F_S(r \cdot phi) = F_{Smax}(r) * w(phi)$$
$$= \text{Phase}(r, phi)$$
$$= \text{Phase}_{max}(r) * w(phi),$$

with $$\text{Phase}_{max}(r) = \sum_{j=2}^{N} k_j * r^j \text{ or } \text{Phase}_{max}(r) = \sum_{j=1}^{N} k_j * r^{2*j},$$

where the radius r changes continuously between 0 and D/2 and the azimuth angle phi of the aperture changes continuously between 0 and $2\pi$, as a result of which the optical grating has a spiral phase profile.

8. The lens as claimed in claim 4, characterized in that the focal power component with the spiral profile $F_S(r, phi)$ emerges from the effect of an optical grating applied to a manufactured second optical surface with the focal power $F_L$, where $$F_G(r, phi) = F_L + F_S(r, phi) = F_L + \text{Phase}(r, phi)$$

applies, and the frequency of the optical grating changes nonlinearly dependent on the radius and dependent on the azimuth angle phi of the aperture, starting from a base value zero to a maximum value $\text{Phase}_{max}$ which supplies the maximum focal power $F_{Smax}(r, phi)$, wherein the following applies to the spiral focal power profile:

$$F_S(r, phi) = F_{Smax}(r, phi) * w(phi)$$
$$= \text{Phase}(r, phi)$$
$$= \text{Phase}_{max}(r, phi) * w(phi),$$

with $$\text{Phase}_{max}(r, phi) = \sum_{j=2}^{N} k_j(phi) * r^j$$

or $$\text{Phase}_{max}(r, phi) = \sum_{j=1}^{N} k_j(phi) * r^{2*j},$$

where the radius r changes continuously between 0 and D/2 and the azimuth angle phi of the aperture changes continuously between 0 and $2\pi$, as a result of which the optical grating has a spiral phase profile.

9. The lens as claimed in claim 3, characterized in that the focal power component with the spiral profile $F_S$ emerges from an additive or subtractive refractive index distribution $\Delta n(r, phi)$, wherein the material of the lens has a refractive index distribution which changes nonlinearly dependent on the radius, starting from a base value $n_2$ to a maximum value $\Delta n_{max}$, where $$F_G(r,phi)=F_L+F_S(r,phi)=F_L+\Delta n(r,phi)$$

applies and the following applies to the spiral focal power profile:

$$F_S(r, phi) = F_{Smax}(r) * w(phi)$$
$$= \Delta n(r, phi)$$
$$= \Delta n_{max}(r) * w(phi),$$

with $$\Delta n_{max}(r) = \sum_{j=2}^{N} c_j * r^j \text{ or } \Delta n_{max}(r) = \sum_{j=1}^{N} c_j * r^{2*j},$$

where the radius r changes continuously between 0 and D/2 and the azimuth angle phi of the aperture changes continuously between 0 and $2\pi$, as a result of which a spiral refractive index distribution of the lens material is described.

10. The lens as claimed in claim 4, characterized in that the focal power component with the spiral profile $F_S$ emerges from an additive or subtractive refractive index distribution $\Delta n(r, phi)$, wherein the material of the lens has a refractive index distribution, which changes nonlinearly dependent on the radius and dependent on the azimuth angle phi of the aperture, starting from a base value $n_2$ to a maximum value $\Delta n_{max}$, where $$F_G(r,phi)=F_L+F_S(r,phi)=F_L+\Delta n(r,phi)$$

applies and the following applies to the spiral focal power profile:

$$F_S(r, phi) = F_{Smax}(r, phi) * w(phi)$$
$$= \Delta n(r, phi)$$
$$= \Delta n_{max}(r, phi) * w(phi),$$

with $$\Delta n_{max}(r, phi) = \sum_{j=2}^{N} c_j(phi) * r^j \text{ or}$$

$$\Delta n_{max}(r, phi) = \sum_{j=1}^{N} c_j(phi) * r^{2*j},$$

where the radius r changes continuously between 0 and D/2 and the azimuth angle phi of the aperture changes continuously between 0 and $2\pi$, as a result of which a spiral refractive index distribution of the lens material is described.

11. A lens system with an extended range of focus, characterized in that the lens with the extended range of focus of claim 1 is arranged in a beam path of the lens system as an imaging element.

12. A lens system with an extended range of focus, characterized in that the lens with the extended range of focus of claim 2 is arranged in a beam path of the lens system as an imaging element.

* * * * *